United States Patent
Smith

(10) Patent No.: US 10,583,263 B2
(45) Date of Patent: Mar. 10, 2020

(54) RESPIRATORY ASSISTANCE APPARATUS

(71) Applicants: Fisher & Paykel Healthcare Limited, Auckland (NZ); Malcolm David Smith, Auckland (NZ)

(72) Inventor: Malcolm David Smith, Auckland (NZ)

(73) Assignee: Fisher & Paykel Healthcare Limited, Auckland (NZ)

(*) Notice: Subject to any disclaimer, the term of this patent is extended or adjusted under 35 U.S.C. 154(b) by 794 days.

(21) Appl. No.: 14/423,073

(22) PCT Filed: Jul. 29, 2013

(86) PCT No.: PCT/NZ2013/000134
§ 371 (c)(1),
(2) Date: Feb. 20, 2015

(87) PCT Pub. No.: WO2014/031010
PCT Pub. Date: Feb. 27, 2014

(65) Prior Publication Data
US 2015/0250962 A1 Sep. 10, 2015

Related U.S. Application Data

(60) Provisional application No. 61/692,428, filed on Aug. 23, 2012.

(51) Int. Cl.
*A61M 16/00* (2006.01)
*A61M 16/16* (2006.01)
(Continued)

(52) U.S. Cl.
CPC .... *A61M 16/0066* (2013.01); *A61M 16/0003* (2014.02); *A61M 16/0012* (2014.02);
(Continued)

(58) Field of Classification Search
CPC .... A62B 7/00; A62B 7/04; A62B 7/14; A62B 18/00; A62B 18/10; A62B 9/00;
(Continued)

(56) References Cited

U.S. PATENT DOCUMENTS 4,651,731 A * 3/1987 Vicenzi ................. A61M 16/00
128/204.25
5,398,676 A * 3/1995 Press ................... A61M 16/0051
128/204.18
(Continued)

FOREIGN PATENT DOCUMENTS

CN 100522278 C 8/2009
EP 1852137 A1 11/2007
(Continued)

OTHER PUBLICATIONS

International Search Report; PCT/NZ2013/000134; dated Oct. 21, 2013; 3 pages.

*Primary Examiner* — Samchuan C Yao
*Assistant Examiner* — Ned T Heffner
(74) *Attorney, Agent, or Firm* — Knobbe, Martens, Olson & Bear, LLP

(57) ABSTRACT

A respiratory assistance apparatus includes a conduit connecting a flow generator and an outlet. The conduit includes a venturi formation. The apparatus further includes an oxygen inlet in fluid communication or selective fluid communication with an oxygen outlet. The oxygen outlet is directed into the conduit and toward a mouth of the venturi formation. The flow generator provides a flow path for air to enter the conduit when the flow generator is not operating.

21 Claims, 4 Drawing Sheets

(51) Int. Cl.
  *A61M 16/12* (2006.01)
  *A61M 16/10* (2006.01)
  *A61M 16/06* (2006.01)

(52) U.S. Cl.
  CPC ...... *A61M 16/0666* (2013.01); *A61M 16/109* (2014.02); *A61M 16/127* (2014.02); *A61M 16/16* (2013.01); *A61M 16/0069* (2014.02); *A61M 16/107* (2014.02); *A61M 16/1095* (2014.02); *A61M 2016/0027* (2013.01); *A61M 2016/0039* (2013.01); *A61M 2016/1025* (2013.01); *A61M 2202/0208* (2013.01); *A61M 2205/3334* (2013.01); *A61M 2205/3368* (2013.01); *A61M 2205/3553* (2013.01); *A61M 2205/502* (2013.01); *A61M 2205/82* (2013.01); *A61M 2205/8206* (2013.01)

(58) Field of Classification Search
  CPC ............. A62B 9/02–027; A61M 11/00; A61M 11/001; A61M 11/02; A61M 11/04; A61M 11/041–048; A61M 16/00–0096; A61M 16/08–0891; A61M 16/16–168; A61M 16/20–208
  See application file for complete search history.

(56) References Cited

U.S. PATENT DOCUMENTS

2005/0051168 A1\* 3/2005 DeVries ............ A61M 16/0051
                                                128/204.21
2005/0115566 A1   6/2005 Van Den Akker et al.
2010/0300446 A1\* 12/2010 Nicolazzi ............ A61M 16/208
                                                128/205.24

FOREIGN PATENT DOCUMENTS

FR            2693117 A1   1/1994
WO    WO 2004/009169 A1   1/2004

\* cited by examiner

RESPIRATORY ASSISTANCE APPARATUS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

The present invention relates to oxygen respiratory therapy apparatus, and in particular, but not exclusively, to a high flow oxygen respiratory therapy apparatus which, in one mode of operation, can be operated independently of an external electricity source.

Background to the Invention

Oxygen respiratory therapy is used when a patient is conscious and no longer requires a ventilator, but still needs to be supplied with an above ambient concentration of oxygen.

In high flow oxygen respiratory therapy, ambient air, to which additional oxygen has been added, is supplied to the patient at a flow rate which is higher than the average rate at which the patient is breathing. The flow rate is intended to be around the same as the maximum instantaneous flow rate during inspiration.

Typically the apparatus used to supply the air/oxygen mixture to the patient is powered by a mains power connection. The apparatus may also receive oxygen from a static oxygen supply. These connections mean that the apparatus is essentially immobile when in use.

However, patients for whom this type of therapy is prescribed may benefit from the ability to leave their bed and move around to some degree, while still receiving oxygen enriched air.

It would also be advantageous if the apparatus could continue to supply the patient with an enriched air supply even in the event of a power failure or a malfunction of the pump which is supplying the air.

The reference to any prior art in the specification is not, and should not be taken as, an acknowledgement or any form of suggestion that the prior art forms part of the common general knowledge in any country.

It is an object of the present invention to provide an oxygen respiratory therapy apparatus which will overcome or ameliorate problems with such apparatus of the prior art, or at least one which will provide a useful choice.

Other objects of the present invention may become apparent from the following description, which is given by way of example only.

SUMMARY OF THE INVENTION

According to one aspect of the present invention there is provided a respiratory assistance apparatus comprising a conduit connecting a flow generator and an outlet, the conduit comprising a venturi formation, the apparatus further comprising a oxygen inlet in fluid communication or selective fluid communication with an oxygen outlet, the oxygen outlet directed into the conduit and toward a mouth of the venturi formation, wherein the flow generator provides a flow path for air to enter the conduit when the flow generator is not operating.

According to a second aspect of the present invention there is provided a respiratory assistance apparatus comprising a conduit connecting a flow generator and an outlet, the conduit comprising a venturi formation, the apparatus further comprising an oxygen inlet in fluid communication or selective fluid communication with an oxygen outlet, the oxygen outlet directed into the conduit and toward a mouth of the venturi formation, wherein the flow generator provides a flow path of air to enter the conduit when the flow generator is not operating, and wherein the apparatus comprises a humidifier between the venturi formation and the outlet.

Preferably, the oxygen outlet directs a jet of oxygen toward the centre of the mouth of the venturi when in use.

Preferably the apparatus comprises a second oxygen outlet in selective fluid communication with the oxygen inlet.

Preferably the second oxygen outlet is provided at a throat of the venturi.

According to a third aspect of the present invention there is provided a method of operating a respiratory assistance apparatus comprising, in a first mode of operation, operating an flow generator to pump air to an outlet of the apparatus, and in a second mode of operation, wherein the flow generator is not operating, directing a jet of oxygen towards a venturi formation, thereby drawing air through the flow generator and forming a combined oxygen/air flow to the outlet of the apparatus.

Preferably the method further comprises the step of adding oxygen to the air when in the first mode of operation.

The invention may also be said broadly to consist in the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

According to a further aspect there are provided respiratory assistance apparatus and methods of operating respiratory assistance apparatus and methods of operating respiratory assistance apparatus according to the attached claims.

According to a still further aspect of the present invention, a oxygen respiratory therapy apparatus and/or a method of operating a oxygen respiratory therapy apparatus is substantially as herein described, with reference to the accompanying drawing.

Further aspects of the invention, which should be considered in all its novel aspects, will become apparent from the following description given by way of example of possible embodiments of the invention.

DETAILED DESCRIPTION OF PREFERRED EMBODIMENTS

Figure 1:
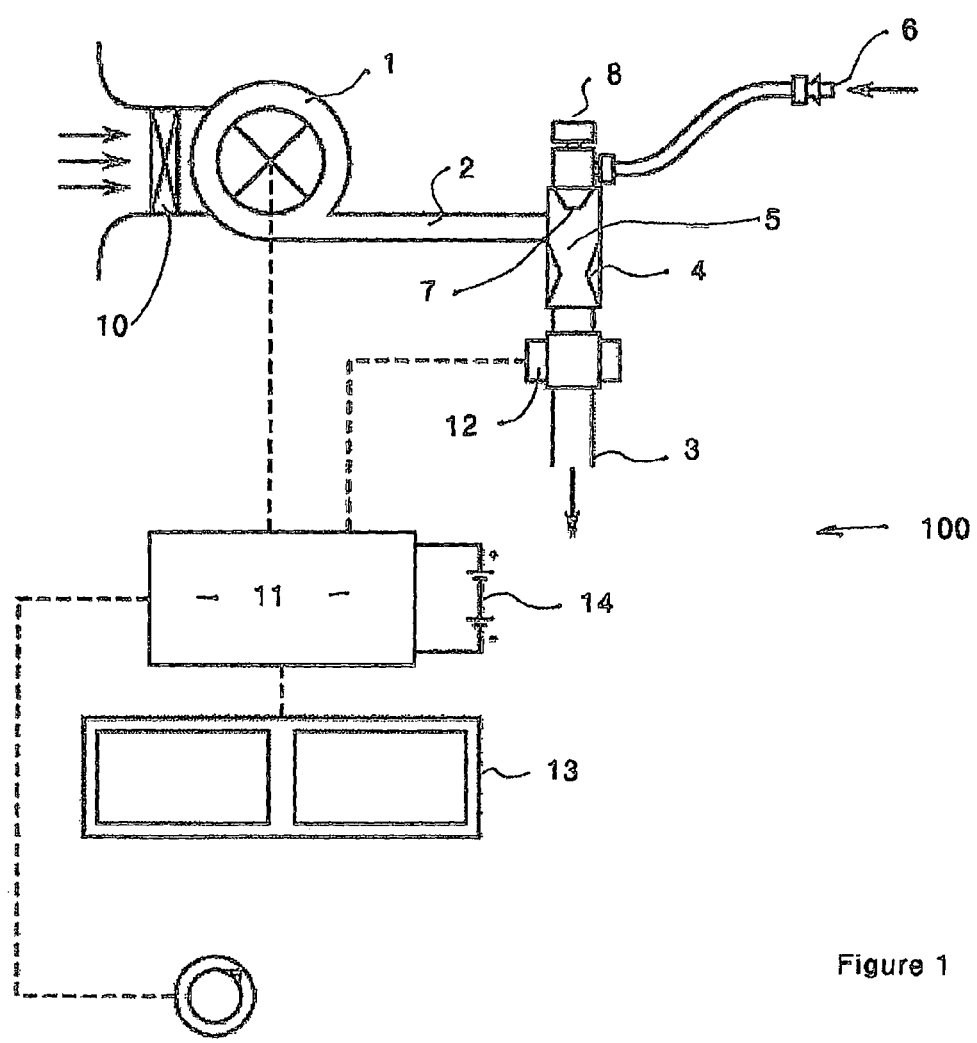
FIG. 1 is a schematic drawing of an oxygen respiratory therapy apparatus of the present invention.
Figure 2:
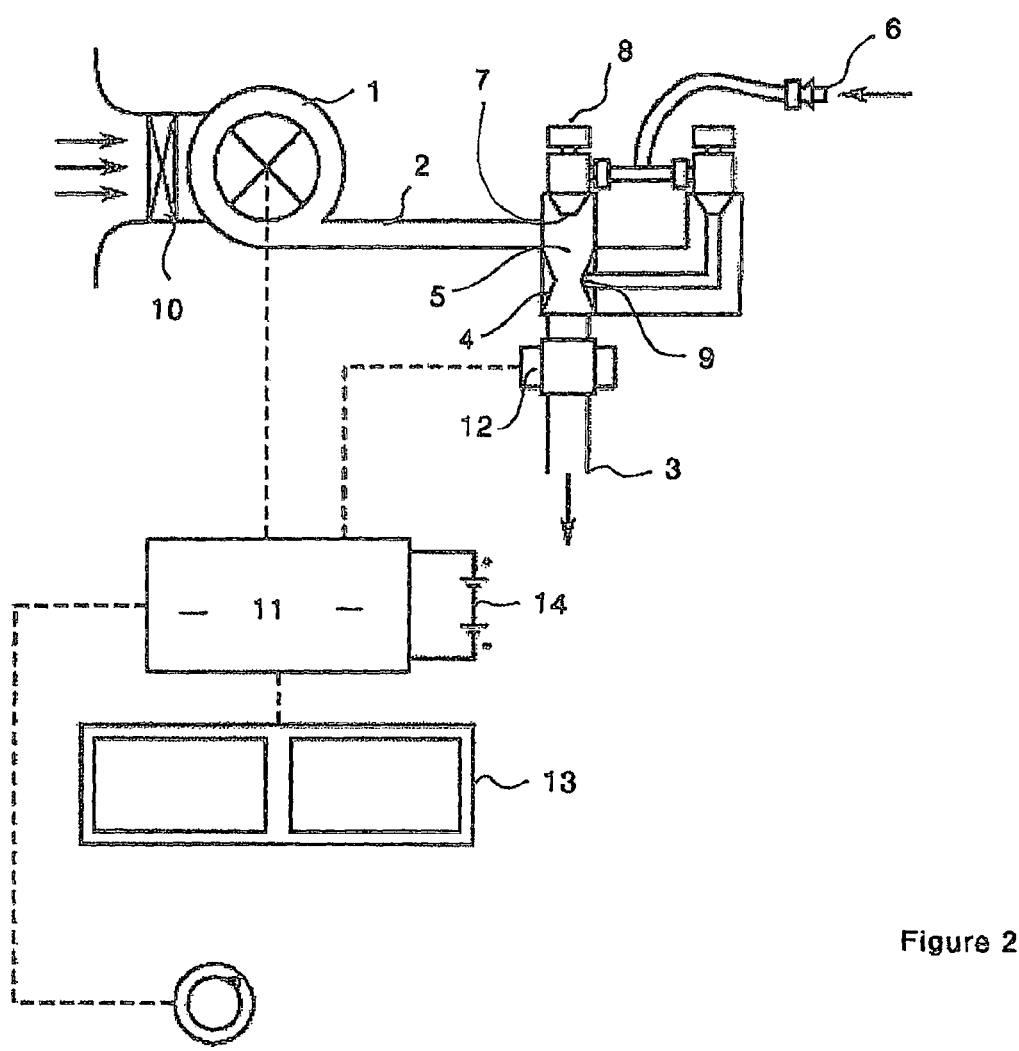
FIG. 2 is a schematic drawing of an oxygen respiratory therapy apparatus of the present invention with an optional second oxygen inlet.

Referring to FIG. 1, a respiratory assistance apparatus of the present invention is generally referenced by arrow 100.

The apparatus 100 comprises a flow generator 1. The flow generator 1 typically comprises a fan or impeller that is rotatably driven by a variable speed motor, and can comprise a centrifugal pump. In preferred embodiments, the flow generator 1 can generate flow rates of at least about 5 litres per minute, or of at least about 10 litres per minute, or of at least about 15 litres per minute, or of at least about 20 litres per minute, or of at least about 25 litres per minute, or of at least about 30 litres per minute, or of at least about 35 litres per minute, or of at least about 40 litres per minute, or of at least about 45 litres per minute, or of at least about 50 litres per minute, or of at least about 60 litres per minute, or of at least about 70 litres per minute, or of at least about 80 litres per minute. In some embodiments, a filter 10 may be connected to the flow generator 1 such that incoming air may be filtered.

The flow generator 1 supplies air to an intake conduit 2.

The intake conduit 2 has an outlet 3 to which a patient interface (not shown) may be connected, typically via a further flexible conduit and/or further conditioning equipment. Any suitable patient interface may be used, for example nasal cannulas or nasal masks. In some embodiments, the patient interface can be selected from the group consisting of: a nasal cannula, such as the OPTIFLOW nasal cannula manufactured by Fisher & Paykel Healthcare Limited of New Zealand; a nasal mask, such as the OPUS nasal pillows mask manufactured by Fisher & Paykel Healthcare Limited of New Zealand; a full-face mask, such as the FREEMOTION full-face mask manufactured by Fisher & Paykel Healthcare Limited of New Zealand; a tracheostomy interface, such as the DIRECTCONNECT tracheostomy interface manufactured by Fisher & Paykel Healthcare Limited of New Zealand.

The intake conduit 2 is provided with a venturi formation 4 located between the flow generator 1 and the outlet 3. The venturi formation 4 has a mouth 5 at an upstream end (that is, fluidically connected to the flow generator 1).

The apparatus 100 has an oxygen inlet 7 which is in fluid communication, or at least selective fluid communication, with an oxygen supply 6. In a preferred embodiment, an adjustable flow controller 8, for example a needle valve, is provided in the flow path between the oxygen supply 6 and the oxygen inlet 7. In preferred embodiments, the adjustable flow controller 8 may be manually adjustable, but, as is described further below, in other embodiments it may be electronically adjustable.

The oxygen inlet 7 can be positioned and orientated towards the venturi mouth 5, such that a jet of oxygen issuing, in use, from the inlet 7, is directed into the venturi 4, preferably directly into the centre of the venturi mouth 5.

As will be appreciated by those skilled in the art, in use the jet of oxygen issuing from the inlet 7 will tend to entrain air through the venturi 4. Accordingly, in some embodiments, a vent or the like may be provided near the venturi mouth 5 to provide a source of ambient air to be entrained. In preferred embodiments, the flow generator 1 is adapted to allow air to be entrained there through.

In a preferred embodiment the apparatus 100 is mountable to, or comprises, a wheeled chassis.

The apparatus 100 may be used in two modes.

In a first mode, the flow generator 1 is powered by a mains power connection and pumps ambient air into the intake conduit 2. The pressure and/or flow rate of the ambient air supplied by the flow generator 1 may be adjusted depending on the patient's requirements, but may typically be in the range 0-100 litres/minute, such as about 10 litres per minute, or about 15 litres per minute, or about 20 litres per minute, or about 25 litres per minute, or about 30 litres per minute, or about 35 litres per minute, or about 40 litres per minute, or about 45 litres per minute, or about 50 litres per minute, or about 60 litres per minute, or about 70 litres per minute, or about 80 litres per minute, and at a pressure of between 0-50 cm $H_2O$, such as about 5 cm $H_2O$, or about 10 cm $H_2O$, or about 15 cm $H_2O$, or about 20 cm $H_2O$, or about 25 cm $H_2O$, or about 30 cm $H_2O$, or about 35 cm $H_2O$, or about 40 cm $H_2O$, or about 45 cm $H_2O$, or about 50 cm $H_2O$.

The oxygen supply 6 is connected to a pressurised oxygen source, for example a centralised oxygen supply or an oxygen bottle. The flow rate of oxygen from the oxygen supply 6 may be adjusted to suit the patient's requirements, but will typically be such that the oxygen comprises between 21% and 100% of the total volume of gas supplied to the patient.

In a second mode, the flow generator 1 is not operational. This may be a result of a fault in the pump, a loss of mains power, or because the patient wishes to move the apparatus 100 away from the bed, such that it is not possible or not desirable to have the apparatus 100 connected to the mains power.

In the second mode, the oxygen flowing from the inlet 7 into the venturi 4 creates an area of below ambient pressure which draws ambient air through the flow generator 1. The flow generator 1 may be configured to minimise the resistance to the ambient air flow in this mode of operation, and may comprise an impeller which offers relatively low resistance to air flow between the pump inlet and outlet when stationary.

If the patient desires to move around then the oxygen supply 6 may be connected to a bottle of pressurised oxygen which, in a preferred embodiment, may be mounted to the apparatus 100. In this way the patient can receive a source of oxygen enriched air while moving around. This may be beneficial in encouraging the patient to maintain or regain mobility after a period of enforced bed rest.

In some embodiments, the apparatus 100 can be provided with a controller 11 which can be in communication with one or more sensors 12. The sensors 12 can include: one or more pressure sensors; one or more flow rate sensors; one or more temperature sensors; one or more oxygen concentration sensors.

In some embodiments, the apparatus 100 can also include a display unit 13 on the apparatus. The display unit 13 can be adapted to show measurements from one or more of the sensors 12. Additionally or alternatively, the measurements can be communicated to a remote monitoring station using known wired or wireless communications methods.

A portable power source 14, such as a battery, may be provided to enable the sensors 12 and/or display unit 13 to function, or at least to generate alerts or alarms, when the apparatus 100 is disconnected from the mains. The size and capacity of the portable power source 14 can be much smaller than would be required to power the pump 1 for a substantial length of time.

If the flow generator 1 ceases operating unexpectedly then the controller 11 may sound an alarm to alert the patient and/or medical staff. However, the patient will still be supplied with a flow of oxygen enriched air. Although the flow rate of oxygen through the inlet 7 (and hence the flow rate of oxygen enriched air) may be increased if desired, this may not be required in some cases.

Those skilled in the art will appreciate that if apparatus 100 has only a single oxygen inlet 7 then the range of oxygen enrichment in the air supplied to the patient when in the second mode of operation will be relatively limited. However, in an alternative embodiment the apparatus 100 may be provided with a second oxygen inlet 9. The second inlet 9 may be provided upstream of the venturi 4, but is preferably not orientated directly towards the mouth 5 of the venturi 4, so that a flow of oxygen through the second oxygen inlet 9 does not cause a corresponding increase in the flow rate of the ambient air. In a preferred embodiment the second oxygen inlet 9 is directed substantially orthogonally to the direction of air flow in its immediate vicinity, and more preferably is provided in the wall of the venturi 4 at the throat.

When in the second mode, oxygen flowing through the second inlet 9 can be used to increase the concentration of oxygen in the combined flow supplied to the patient.

Figure 3:
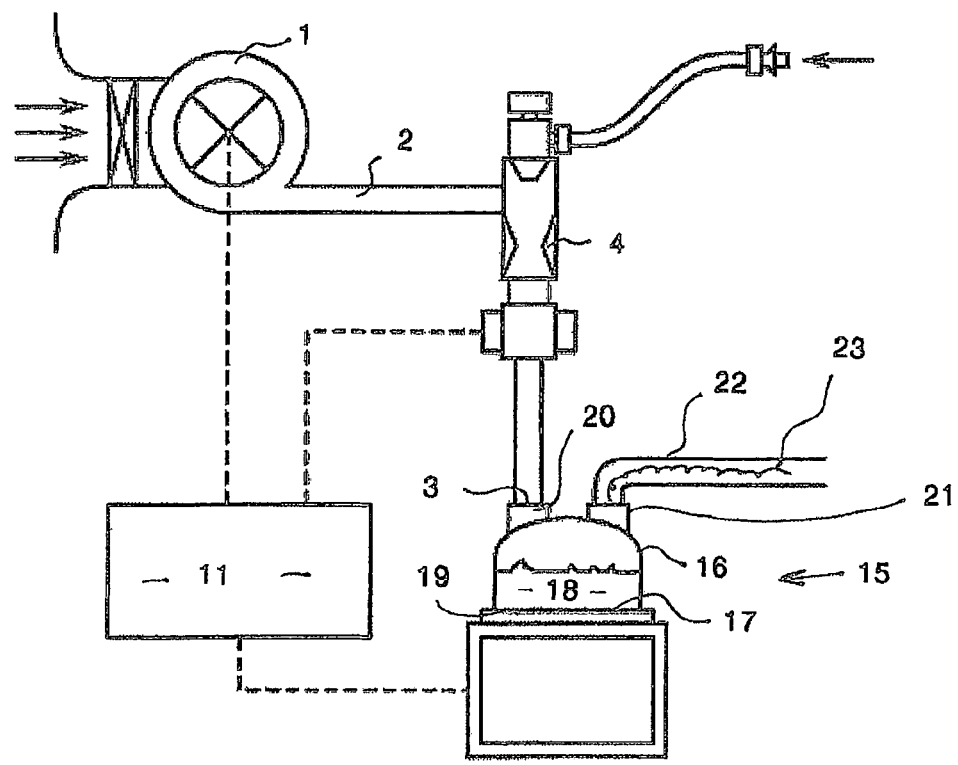
FIG. 3 is a schematic drawing of the oxygen respiratory therapy apparatus of FIG. 1 connected to a humidification apparatus.

Referring next to FIG. 3, in a preferred embodiment the apparatus 100 is connectable to a humidification apparatus 15. An exemplary humidification apparatus 15 is described in U.S. Pat. No. 6,349,722, the contents of which are included herein in their entirety by reference. In some embodiments, the humidification apparatus 15 can be one of the MR810, MR850, MR880 humidifiers, all manufactured by Fisher & Paykel Healthcare Limited of New Zealand.

The humidification apparatus 15 preferably comprises a chamber 16 which holds a volume of humidification fluid 18 (which can be water). The chamber 16 can be formed of a plastic material, and will preferably have a thermally conductive base 17 (such as a metal base) connected thereto. The chamber 16 can be thermally coupled to a heater 19, which, in use, heats the humidification fluid 18 within the chamber 16 to increase its rate of evaporation.

The chamber has an inlet 20 which is connectable to the outlet 3 of conduit 2, and an outlet 21 which is connectable to a patient interface, typically via a flexible conduit 22. In preferred embodiments, the conduit 22 comprises an integral heating means to reduce the risk of condensation in the conduit 22. The heating means is typically a heater wire 23. The heater wire 23 can be disposed within the gas path of the conduit 22, can be located within the wall of the conduit 22, can be wrapped helically around the outside of the conduit 22, and/or any other suitable means as is known in the art.

A controller controls the heat input into the humidification fluid 18 from the heater 19, in order to generate a required level of humidity in the gases stream at the outlet 21. In a preferred embodiment the controller 11 may be adapted to communicate with and/or control the humidification apparatus 15. The communication may be by any suitable wireless protocol, or there may be a wired connection between the humidification apparatus 15 and the oxygen respiratory therapy apparatus controller 11. In one embodiment the humidification inlet 20 and the outlet 3 may be provided with respective complementary sockets and plugs, so that an electrical connection is established between the controller 11 and the humidification apparatus 15 at the same time as the gases flow path is established between them.

Figure 4:
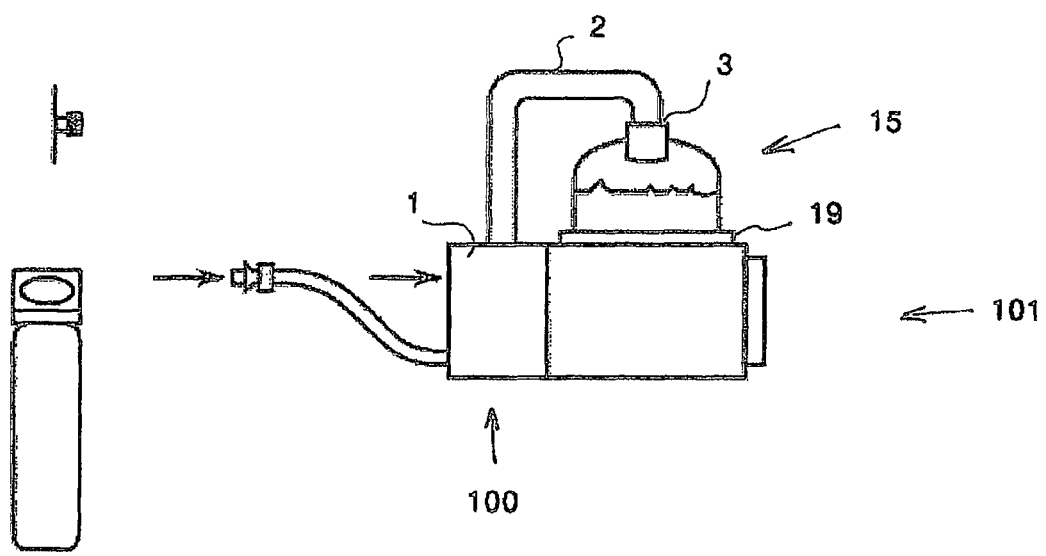
FIG. 4 is a schematic drawing of an oxygen respiratory therapy apparatus of the present invention with an integrated humidification apparatus.

Referring next to FIG. 4, in another embodiment, generally referenced 101, the apparatus 100 and the humidification apparatus 15 may be incorporated into a single integrated unit. In this embodiment the portable power source 14 (not shown in FIG. 4), if provided, may also power the heater 19 for a period of time if the mains power source is interrupted for any reason. In some embodiments the controller 11 may allow the humidity at the outlet 21 and/or the temperature of the gas at the outlet 21 to drop to a lower level if the mains power is interrupted, so that the power consumed by the heater 19 is reduced. The heater wire 23 may also be powered when the mains power is interrupted, although possibly at a lower power level. However, if the controller lowers the humidity of the gas leaving the humidification apparatus 15 then, depending on the ambient temperature, it may not be necessary to power the heater wire at all. In such a case the controller may switch off the power to the heater wire in order to conserve power.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Where in the foregoing description, reference has been made to specific components or integers of the invention having known equivalents, then such equivalents are herein incorporated as if individually set forth.

Although this invention has been described by way of example and with reference to possible embodiments thereof, it is to be understood that modifications or improvements may be made thereto without departing from the spirit or scope of the invention.

The invention claimed is:

1. A respiratory assistance apparatus comprising a conduit connected to a flow generator, the conduit comprising a venturi formation positioned downstream of the flow generator and an outlet, the apparatus further comprising:
   a first oxygen inlet in fluid communication or selective fluid communication with an oxygen supply, the first oxygen inlet directed into the conduit and directed toward a mouth of the venturi formation; and
   a second oxygen inlet configured to direct oxygen into the conduit;
   wherein the flow generator is configured to operate in a first mode and a second mode, wherein, in the first mode, the flow generator is operational and pumps air through a flow path through the flow generator to the conduit and, wherein, in the second mode, the flow generator is deactivated and offers the flow path for air to enter the conduit when drawn in from a pressure drop caused by oxygen flowing into the venturi formation.

2. The respiratory assistance apparatus of claim 1, wherein the first oxygen inlet directs a jet of oxygen toward the center of the mouth of the venturi formation when in use.

3. The respiratory assistance apparatus of claim 1, wherein the second oxygen inlet is directed into the conduit at a throat of the venturi formation.

4. The respiratory assistance apparatus of claim 1, further comprising an adjustable flow controller disposed between the oxygen supply and the first oxygen inlet.

5. The respiratory assistance apparatus of claim 1, further comprising a controller in communication with one or more sensors.

6. The respiratory assistance apparatus of claim 1, further comprising a display unit adapted to show measurements from one or more sensors.

7. The respiratory assistance apparatus of claim 1, further comprising one or more sensors, wherein measurements from the one or more sensors are communicated to a remote monitoring station.

8. The respiratory assistance apparatus of claim 1, further comprising a portable power source and a controller in communication with one or more sensors, wherein the portable power source provides power to the one or more sensors.

9. The respiratory assistance apparatus of claim 1, further comprising a portable power source and a display unit adapted to show measurements from one or more sensors, wherein the portable power source provides power to the one or more sensors and the display unit.

10. The respiratory assistance apparatus of claim 1, further comprising a portable power source and one or more sensors, wherein measurements from the one or more sensors are communicated to a remote monitoring station and the portable power source provides power to the one or more sensors.

11. The respiratory assistance apparatus of claim 1, further comprising a portable power source, wherein the portable power source provides power to the humidifier.

12. The respiratory assistance apparatus of claim 1, wherein the venturi formation includes an outlet and the second oxygen inlet is provided between the first oxygen inlet and the outlet of the venturi formation.

13. The respiratory assistance apparatus of claim 1, wherein the apparatus further comprises a humidifier, the humidifier comprises a chamber, the chamber comprises an inlet and an outlet, and the inlet of the humidifier is connected to the outlet of the conduit.

14. The respiratory assistance apparatus of claim 13, further comprising a controller in communication with the humidifier.

15. The respiratory assistance apparatus of claim 1, wherein the second oxygen inlet is provided upstream of the venturi formation but is not oriented to direct flow directly towards the mouth of the venturi formation.

16. The respiratory assistance apparatus of claim 15, wherein the second oxygen inlet is directed orthogonally to the direction of air flow in an immediate vicinity of the second oxygen inlet.

17. The respiratory assistance apparatus of claim 15, wherein the second oxygen inlet is in fluid communication or selective fluid communication with the oxygen supply.

18. A respiratory assistance apparatus comprising an intake conduit, the intake conduit being configured for connection to a gas flow generator positioned upstream of the intake conduit, the intake conduit comprising a venturi formation positioned downstream of the flow generator, a first oxygen inlet being in fluid communication with the intake conduit at a location upstream of an entrance into the venturi formation, the venturi formation comprising a flow axis along which flow through a throat of the venturi formation takes place, the first oxygen inlet being directed in a direction parallel with the flow axis, a second oxygen inlet configured to direct oxygen into the intake conduit and in fluid communication with the intake conduit at a location downstream of the first oxygen inlet, and the second oxygen inlet being directed in a direction that is not parallel with the flow axis through the throat of the venturi formation; wherein the flow generator is configured to operate in a first mode and second mode, wherein, in the first mode, the flow generator is operational and pumps air through a flow path through the flow generator to to the intake conduit and, wherein, in the second mode, the flow generator is deactivated and offers the flow path for air to enter the intake conduit when drawn in from a pressure drop caused by oxygen flowing into the venturi formation.

19. The respiratory assistance apparatus of claim 18, wherein the second oxygen inlet is configured to direct oxygen into the venturi formation of the intake conduit.

20. The respiratory assistance apparatus of claim 18, wherein the second oxygen inlet opens into the throat of the venturi formation.

21. The respiratory assistance apparatus of claim 20, wherein a single oxygen supply is in fluid communication with both the first oxygen inlet and the second oxygen inlet.

* * * * *

UNITED STATES PATENT AND TRADEMARK OFFICE
CERTIFICATE OF CORRECTION

PATENT NO.      : 10,583,263 B2
APPLICATION NO. : 14/423073
DATED           : March 10, 2020
INVENTOR(S)     : Malcolm David Smith It is certified that error appears in the above-identified patent and that said Letters Patent is hereby corrected as shown below:

In the Claims

Column 8, Line 26, in Claim 18, after "generator" delete "to".

Signed and Sealed this
Twenty-third Day of June, 2020

Andrei Iancu
*Director of the United States Patent and Trademark Office*